(12) United States Patent
Chiang

(10) Patent No.: US 8,187,219 B1
(45) Date of Patent: May 29, 2012

(54) MASSAGING MANUAL BREAST PUMP

(76) Inventor: Yat San Chiang, Hong Kong (CN)

( * ) Notice: Subject to any disclaimer, the term of this patent is extended or adjusted under 35 U.S.C. 154(b) by 0 days.

(21) Appl. No.: 13/113,016

(22) Filed: May 20, 2011

(30) Foreign Application Priority Data

Jan. 8, 2011 (CN) .......................... 2011 1 0002922

(51) Int. Cl.
*A61M 1/06* (2006.01)
(52) U.S. Cl. ................................ 604/74; 604/73; 604/75
(58) Field of Classification Search ............... 604/73–76
See application file for complete search history.

(56) References Cited

U.S. PATENT DOCUMENTS

| | | | |
|---|---|---|---|
| 2004/0249340 A1* | 12/2004 | Britto et al. ...................... | 604/74 |
| 2006/0111664 A1* | 5/2006 | Samson et al. ................... | 604/74 |
| 2007/0078383 A1* | 4/2007 | Tashiro et al. ................... | 604/74 |
| 2008/0195039 A1* | 8/2008 | Kataoka et al. .................. | 604/74 |
| 2009/0062731 A1* | 3/2009 | Keyong et al. ................... | 604/74 |

* cited by examiner

*Primary Examiner* — Quynh-Nhu H Vu

(57) ABSTRACT

A massaging manual breast pump comprising a pumping assembly, a receptacle, a lid, a handle, and a cushion is provided. The pumping assembly comprises a cavity formed inside of the pumping assembly; a cover extended downwardly from periphery of a bottom of the cavity to define an opening; a receiver disposed at the bottom of the cavity and in communication therewith; a duck mouth valve provided to engage with the receiver at one end and attached to the receptacle at the other end; a pumping insert accommodated in the cavity; an air chamber provided on a top of the pumping insert, with the lid covered on the air chamber; a support extended acclivously from a side wall of the cavity to engage with the handle; a conduit extended acclivously from another side wall of the cavity and in fluid communication with the cavity; a cup formed at one end of the conduit and in a shape of a trumpet for receiving a breast, the cushion being assembled with the cup with a slot disposed therebetween; and a tube connected between the slot and the air chamber.

8 Claims, 6 Drawing Sheets

MASSAGING MANUAL BREAST PUMP

FIELD OF THE INVENTION

The present invention relates to a manual breast pump with massaging effect.

BACKGROUND OF THE INVENTION

CN201375701Y disclosed a true sense massaging breast pump wherein the breast pump has a silica gel liner capable of shrinking and expanding automatically during milking, such that the user would not suffer from breast distending pain and feel comfortable. The disclosed breast pump comprises a pump unit, a breast cup, and a silica gel inner lining, wherein a threaded adaptor is mounted on an upper end of the pump unit and an air vent is provided on the breast cup, with the rear end of the breast cup provided with a threaded hole for coupling with the threaded adaptor. A baffle ring is provided in the threaded hole to cooperate with a flange provided to the bottom of the inner lining. The side walls of the inner lining abutting against breast have a corrugated shape. The disclosed breast pump has a disadvantage of an absence of functions of massaging breast, stimulating areola, and pressing teat cistern during pumping due to the presence of the air vent provided on the cup. In this case, frequent using would cause uncomfortable sensations such as breast ache, inflamed nipple, and breast deformation. The disclosed breast pump has no differences in this respect from conventional breast pumps.

PCT/NO2003/000436 described a manual breast pump comprising a breast cup, a pump housing with a piston and an activation mechanism in the form of a handle, together with a container, preferably in the form of a bottle for collection of the milk. The breast cup comprises a preferably rigid outer part and an inner, preferably completely or partially flexible, part, where two mutually separate chambers are provided between the outer part and the inner part. The piston comprises a membrane that connects the periphery of the piston with the wall of the pump housing and thereby divides the pump housing into an upper chamber and a lower chamber. The upper chamber is in liquid contact with the chambers of the breast cup with the help of two openings with associated tubes and the lower chamber is in liquid contact with the inside of the breast cup. The described manual breast pump has a disadvantage that the breast cup has no action in use and a negative pressure will be generated inside the interior of the breast cup during milking, so as to press the breast to milk, causing breast distending pain.

PCT/IB2005/000044 disclosed a breast pump comprising: a housing having a funnel portion, said funnel portion comprising an outer funnel and an inner funnel received in said outer funnel and said inner funnel defining a funnel interior adapted to sealablely engage a breast; at least one flexible membrane formed in the inner funnel; a chamber defined by an inside wall of said housing, said chamber adapted to receive a pressure generating mechanism and having a vacuum port in fluid communication with said funnel interior and having a pressure port; a pressure conduit in fluid communication with said pressure port and said membrane; wherein during a stroke of said pressure generating mechanism a negative pressure is conveyed to said funnel interior and a positive pressure is conveyed to said pressure conduit to displace said flexible membrane. The breast pump disclosed is capable of massaging the breast while milking. However, the complicated structure of this type makes the breast pump difficult to assemble and clean, non-cost effective, and possibly forms rust.

SUMMARY OF THE INVENTION

An object of the present invention is to provide a massaging manual breast pump that overcomes drawbacks in the prior art. The provided massaging manual breast pump mimics baby's sucking and gently press a user's breast, causing milk expression from the breast while providing a massage thereto.

In order to achieve the above object, a massaging manual breast pump, comprising a pumping assembly, a receptacle, a lid, a handle, and a cushion, wherein the pumping assembly comprises a cavity formed inside of the pumping assembly; a cover extended downwardly from periphery of a bottom of the cavity to define an opening; a receiver disposed at the bottom of the cavity and in communication therewith; a duck mouth valve provided to engage with the receiver at one end and attached to the receptacle at the other end; a pumping insert accommodated in the cavity; an air chamber provided on a top of the pumping insert, with the lid covered on the air chamber; a support extended acclivously from a side wall of the cavity to engage with the handle; a conduit extended acclivously from another side wall of the cavity and in fluid communication with the cavity; a cup formed at one end of the conduit and in a shape of a trumpet for receiving a breast, the cushion being assembled with the cup with a slot disposed therebetween; and a tube connected between the slot and the air chamber.

In a preferable embodiment, the pumping insert comprises an insert accommodated in the cavity through the engagement of a buckling structure of the insert; a recess provided at a bottom of the pumping insert with a mounting hole disposed in the center of the bottom; and a connecting rod abutted against the recess by a transverse rod and penetrated through the mounting hole; wherein the connecting rod further comprises a first notch and a second notch respectively engaged with a groove provided at an end of the handle and the mounting hole of the insert.

Preferably, the cushion is provided with a plurality of openings on its surface with each opening covered by a flexible material, and the cushion is attached to the cup by a hook formed integrally with the cushion, with the flexible material pressed against the breast through pressured air, in order to provide a massaging action which aids in the expression of milk from the breast.

Preferably, a shaft hole is provided to the handle for aligning with a rotating shaft provided at a distal end of the support such that the handle is pivotally connected to the pumping assembly.

In a preferable embodiment, a cap is provided to cover the cushion and the cup for hygiene consideration.

In a preferable embodiment, the handle comprises a crank, the shaft hole, a platform extending substantively perpendicular to the length of the crank at a top end of thereof, and the groove for engagement with the first notch.

Preferably, the cup is in threaded connection with the conduit.

In a preferable embodiment, the cushion is comprised of an inner liner, an outer liner and a slot formed therebetween, and wherein the inner liner comprises a plurality of openings with each opening covered by a flexible material and covers in integrity the cup, and the outer liner is provided with an aperture and covers in integrity the inner liner.

In comparison with conventional product, the present invention has at least the following advantages.

1. The flexible material such as a film presses against the breast, causing milk to be expressed from the breast and providing a massaging action which further aids in the expression of milk from the breast, and enhances comfort for the user.

2. The tube connected between the slot and the air chamber ensures the continuity of massaging effect.

3. The breast pump of the present invention is made of nontoxic and harmless materials which meet the standards of FDA and EN71.

4. The breast pump of the present invention is easy to assemble and use, while ensuring sanitary conditions.

5. The present breast pump provides good impermeability in order to achieve desirable performance.

6. The breast pump is simple to operate and can be disassembled without need of specific tool for cleaning and disinfection.

DETAILED DESCRIPTION OF ILLUSTRATED EMBODIMENTS

Figure 1:
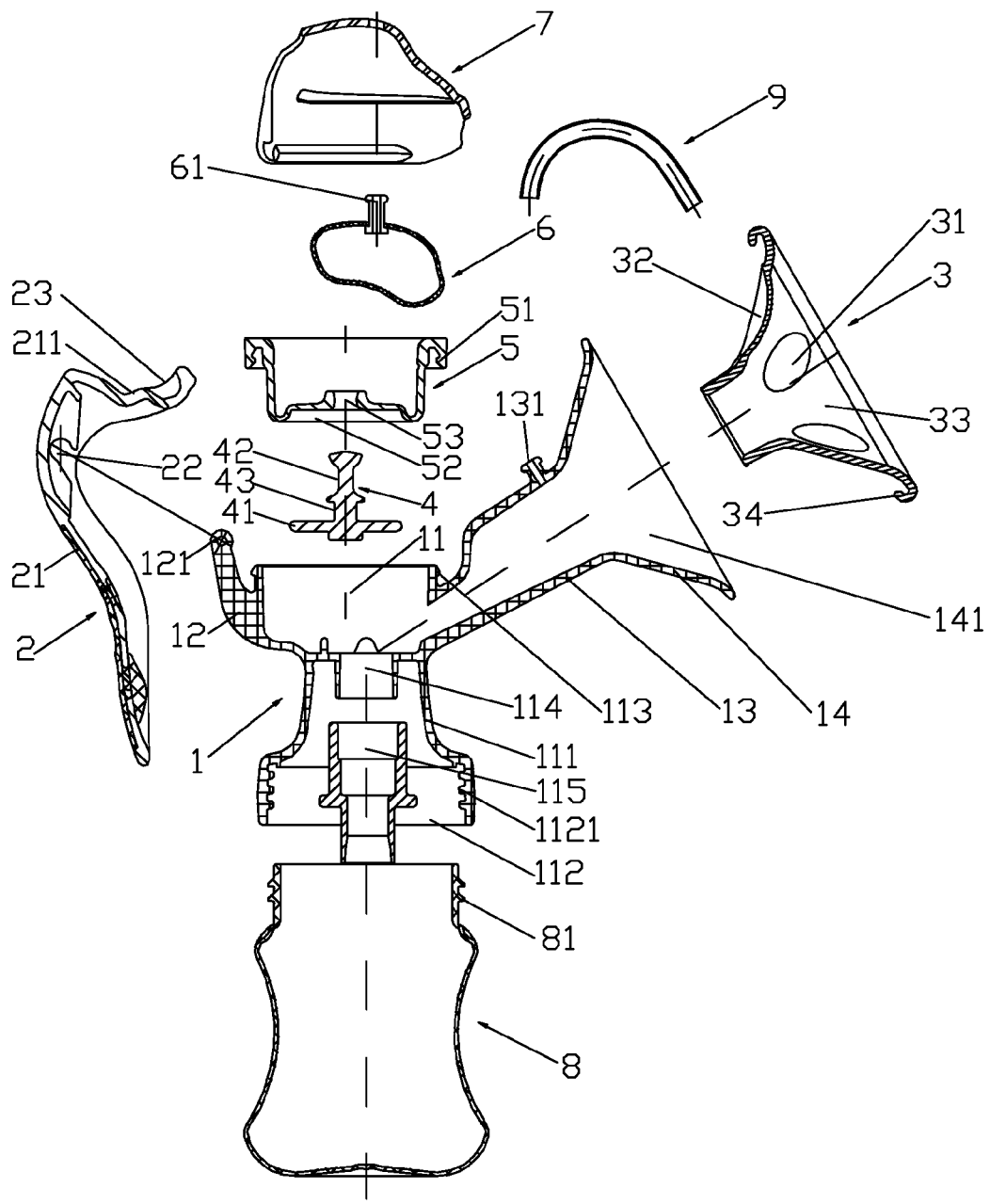
FIG. 1 is an exploded view of the structure of the breast pump according to a first example of the present invention.
Figure 2:
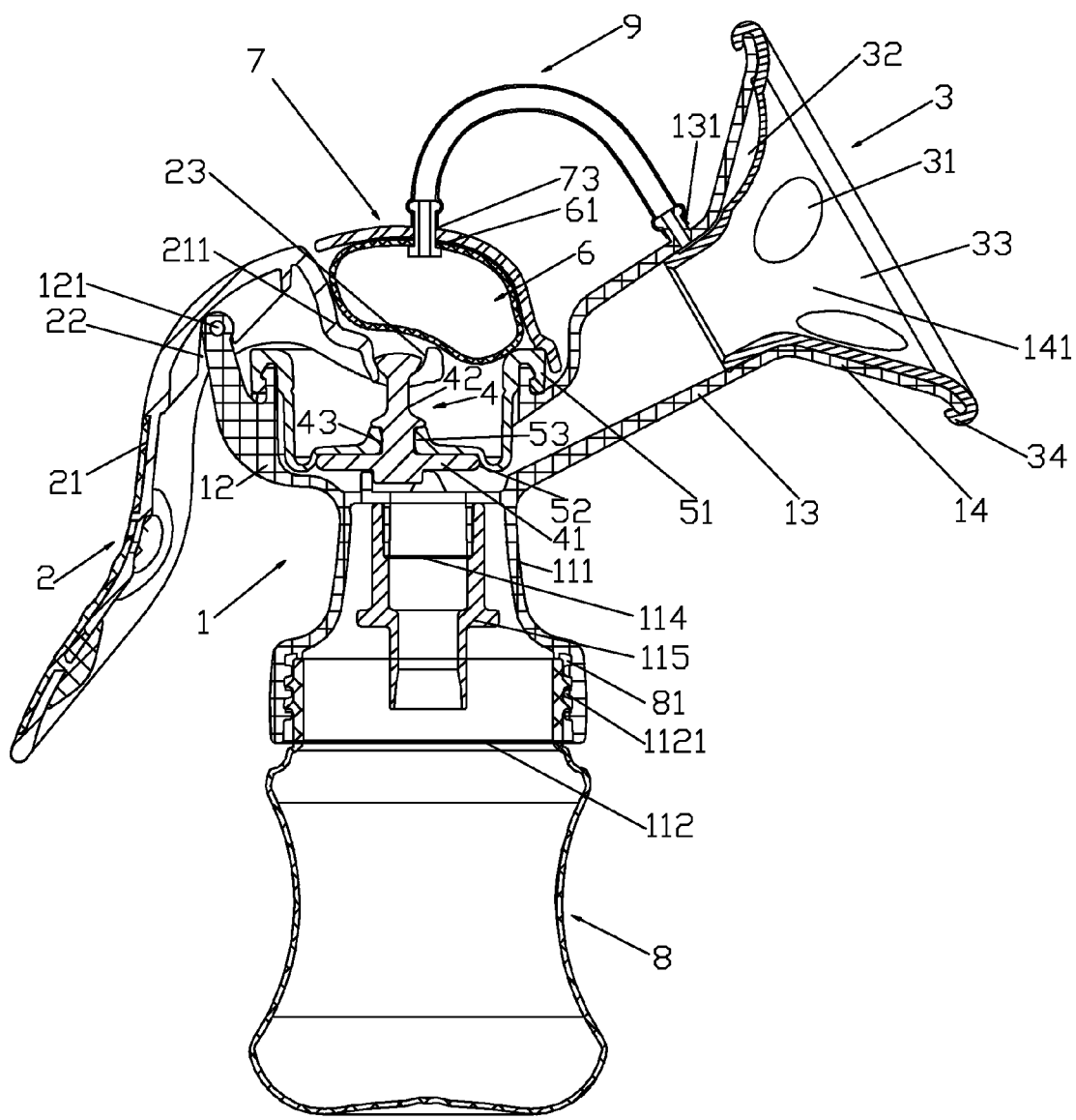
FIG. 2 is an assembled view of the breast pump according to the first example of the present invention.
Figure 3:
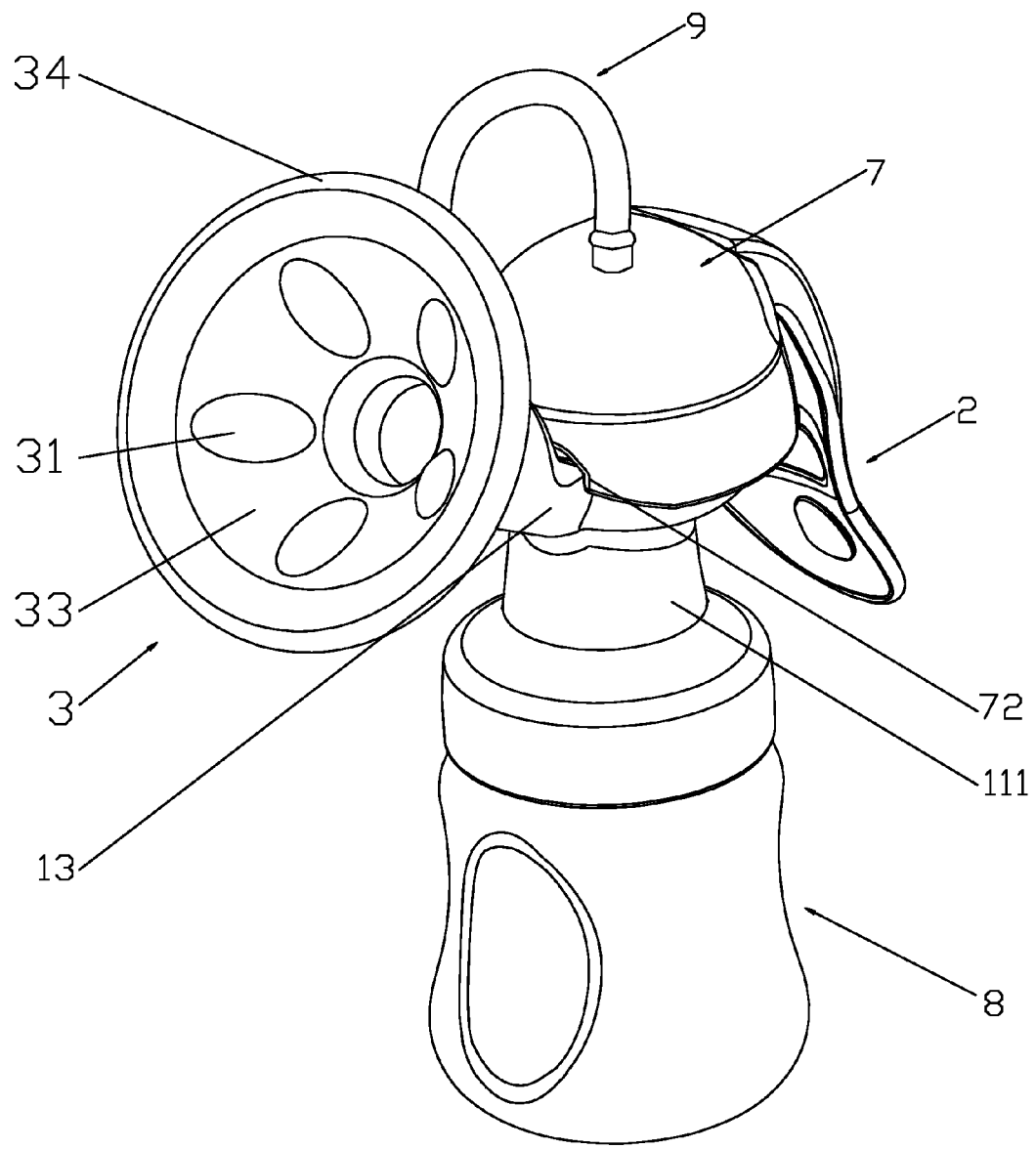
FIG. 3 is a perspective view of the breast pump of the first example of the present invention.
Figure 4:
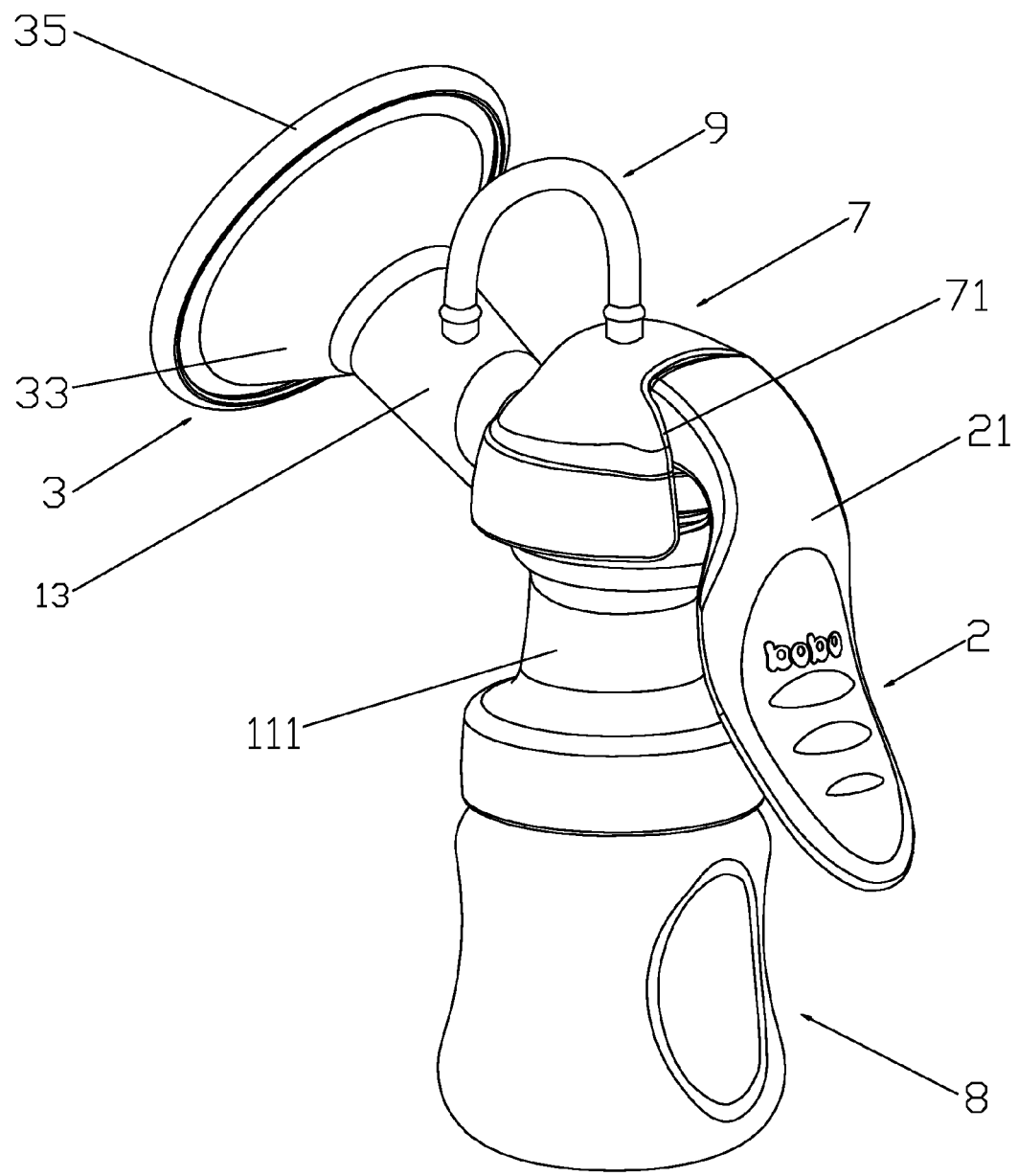
FIG. 4 is another perspective view of the breast pump of the first example of the present invention.

The present invention will be further described with reference to the accompanied drawings.

FIGS. 1-4 show a first embodiment of the present invention.

The massaging manual breast pump in this embodiment comprises a pumping assembly 1, a handle 2 having a platform 211 and a groove 23, a cushion 3, a connecting rod 4 comprising a transverse rod 41, a first notch 42 and a second notch 43, an insert 5, an air chamber 6 having an orifice 61, a lid 7, a receptacle 8 and a tube 9.

The pumping assembly 1 comprises a cavity 11 for accommodating the insert 5, a support 12 extending acclivously from a side wall of the cavity 11, a conduit 13 extending acclivously from another side wall of the cavity 11 and in fluid communication with the cavity 11, a cup 14 formed at one end of the conduit 13 and in a shape of a trumpet for receiving a breast, an aperture 131 disposed in a connection area of the cup and the conduit, a receiver 114 disposed at a bottom of the cavity 11 and in communication therewith, and a cover 111 formed downwardly from a periphery of the bottom of the cavity 11 to define an opening 112 with an inner screw thread 1121 of the cover 111 formed in order to engage with an outer screw thread 81 of the receptacle 8.

The cushion 3 to be assembled into the cup 14 is constructed such that a slot 32 is sandwiched between an inner surface 141 of the cup 14 and an outer surface 33 of the cushion 3. A duck mouth valve 115 is provided to engage with the receiver 114.

The insert 5 is contained in the cavity 11 with the lid 7 covered thereon. The lid 7 is constructed with recessed portions 71 and 72 to match with the handle 2 and the conduit 13 respectively. An air vent 73 is disposed at a top of the lid in order to align with the orifice 61 of the air chamber 6 such that the aperture 131 is in communication and the orifice 61 through the tube 9.

The insert 5 is accommodated in the cavity 11 through the engagement of a buckling structure 51 of the insert 5 and a protrusion 113 of the side walls of the cavity 11. The insert 5 is provided with a recess 52 at the bottom with a mounting hole 53 disposed in the center.

When assembled, the connecting rod 4 abuts against the recess 52 by the transverse rod 41 and penetrates through the mounting hole 53. The first notch 42 is engaged with the groove 23 provided at an end of the handle 2. The second notch 43 is engaged with the mounting hole 53 of the insert 5.

The cushion 3, preferably made of silica gel, is provided with a plurality of openings 31 on its surface with each opening covered by a flexible material, such as bubble-shaped film. The cushion 3 is attached to the cup 14 by a hook 34 formed integrally with the cushion 3. A cap 35 may be provided to cover the cushion 3 and the cup 14 for hygiene consideration.

The handle 2, preferably at least partly covered with rubber, comprises a crank 21, a shaft hole 22 for aligning with a rotating shaft 121 provided at a distal end of the support 12 such that the handle 2 is pivotally connected to the pumping assembly 1, the platform 211 extending substantively perpendicular to the length of the crank 21 at a top end of thereof, and the groove 23 for engagement with the first notch 42.

In operation, the cup 14 receives a user's breast, and the movement of the handle 2 causes the connecting rod 4 to reciprocally move up and down through the engagement of the groove 23 with the first notch 42. The upward movement of the connecting rod 4 causes the upward movement of the insert 5, generating a negative pressure within the pumping assembly 1. In the meantime, the air chamber 6 is pressed by the handle 2, resulting in a reduction in the volume of the air chamber 6 and, in turn, an increase in the pressure inside the air chamber 6. The air in the air chamber 6, due to the increased pressure, flows in sequence through the orifice 61, the air vent 73, the tube 9 and the aperture 131 and then accesses to the cushion 3. The air enters into the openings 31 through the slot 32 and, due to the pressure increase in the air chamber 6 and the negative pressure generated in the pumping assembly 1, forces the flexible material such as films to press against the breast, in order to cause milk to be expressed from the breast and provide a massaging action which further aids in the expression of milk from the breast, and enhances comfort for the user.

When the handle 2 is released, due to the elastic properties of the air chamber 6 and cushion 3 and the rebound of the breast against the film, air returns through the tube 9 back to the air chamber 6 in order to achieve air pressure balance.

Figure 5:
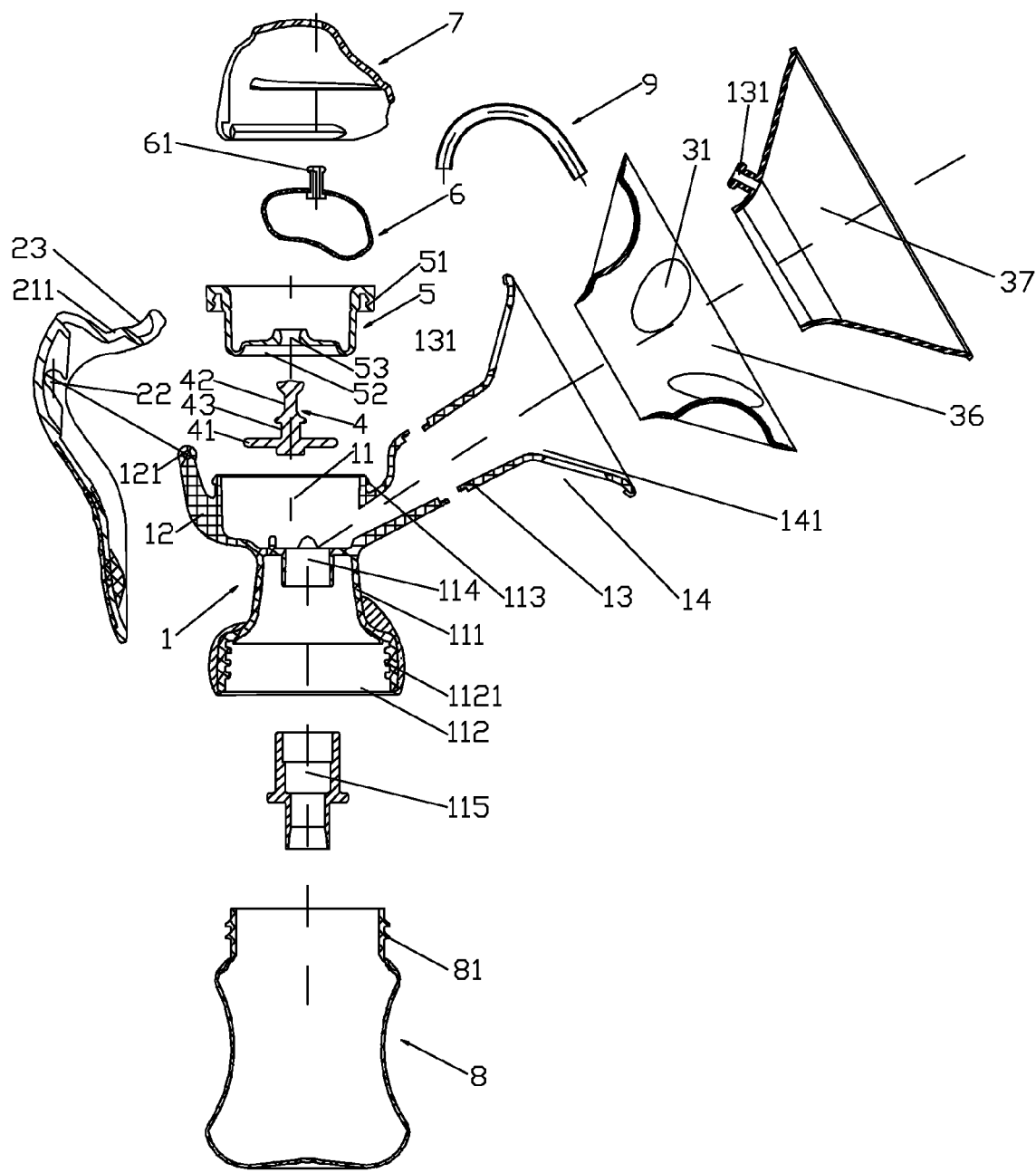
FIG. 5 is an exploded view of the structure of the breast pump according to a second example of the present invention.
Figure 6:
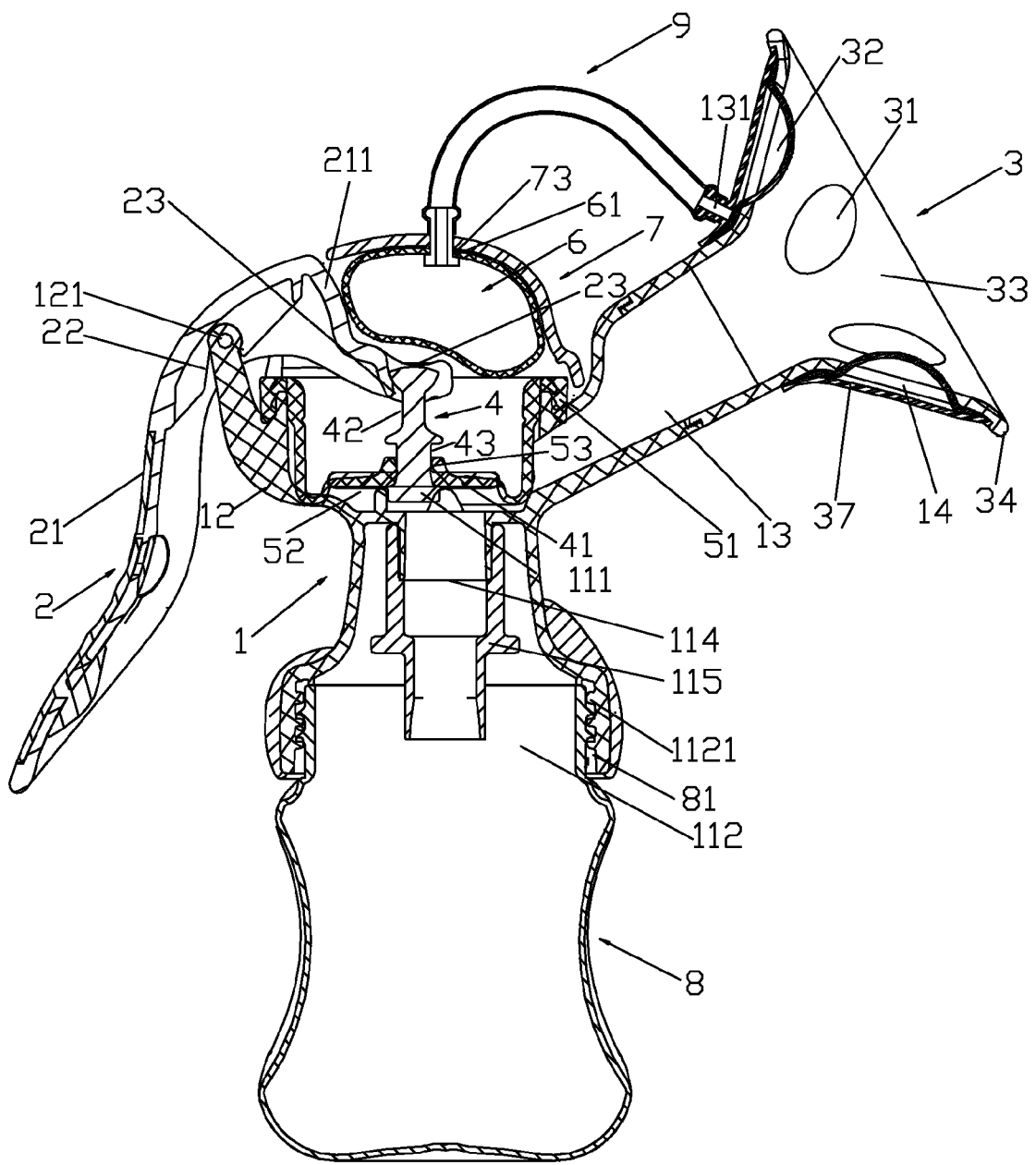
FIG. 6 is an assembled view of the breast pump according to the second example of the present invention.

FIGS. 5-6 show a second embodiment of the present invention.

The second embodiment is substantively the same as the first embodiment except for the following. In the second embodiment, the cup 14 is in threaded connection with the conduit 13. The cushion 3 is comprised of an inner liner 36, an outer liner 37 and a slot 32 formed therebetween. The inner liner 36 comprises a plurality of openings 31 with each opening covered by a flexible material, such as bubble-shaped film, and covers in integrity the cup 14. The outer liner 37 is provided with an aperture 131 and covers in integrity the inner liner 36.

The present invention is described with reference to preferable examples. Any equivalent changes or modifications made based on these examples are included in the scope of the present invention.

What is claimed is:

1. A massaging manual breast pump, comprising a pumping assembly, a receptacle, a lid, a handle, and a cushion, wherein the pumping assembly comprises
   a cavity formed inside of the pumping assembly;
   a cover extended downwardly from periphery of a bottom of the cavity to define an opening;
   a receiver disposed at the bottom of the cavity and in communication therewith;
   a duck mouth valve provided to engage with the receiver at one end and attached to the receptacle at the other end;
   a pumping insert accommodated in the cavity;
   an air chamber provided on a top of the pumping insert, with the lid covered on the air chamber;
   a support extended acclivously from a side wall of the cavity to engage with the handle;
   a conduit extended acclivously from another side wall of the cavity and in fluid communication with the cavity;
   a cup formed at one end of the conduit and in a shape of a trumpet for receiving a breast, the cushion being assembled with the cup with a slot disposed therebetween; and
   a tube connected between the slot and the air chamber.

2. The massaging manual breast pump of claim 1, wherein the pumping insert comprises
   an insert accommodated in the cavity through the engagement of a buckling structure of the insert;
   a recess provided at a bottom of the pumping insert with a mounting hole disposed in the center of the bottom; and
   a connecting rod abutted against the recess by a transverse rod and penetrated through the mounting hole; wherein the connecting rod further comprises a first notch and a second notch respectively engaged with a groove provided at an end of the handle and the mounting hole of the insert.

3. The massaging manual breast pump of claim 1, wherein the cushion is provided with a plurality of openings on its surface with each opening covered by a flexible material, and the cushion is attached to the cup by a hook formed integrally with the cushion, with the flexible material pressed against the breast through pressured air, in order to provide a massaging action which aids in the expression of milk from the breast.

4. The massaging manual breast pump of claim 1, wherein a shaft hole is provided to the handle for aligning with a rotating shaft provided at a distal end of the support such that the handle is pivotally connected to the pumping assembly.

5. The massaging manual breast pump of claim 1, wherein a cap is provided to cover the cushion and the cup for hygiene consideration.

6. The massaging manual breast pump of claim 1, wherein the handle comprises a crank, the shaft hole, a platform extending substantively perpendicular to the length of the crank at a top end of thereof, and the groove for engagement with the first notch.

7. The massaging manual breast pump of claim 1, wherein the cup is in threaded connection with the conduit.

8. The massaging manual breast pump of claim 1, wherein the cushion is comprised of an inner liner, an outer liner and a slot formed therebetween, and wherein the inner liner comprises a plurality of openings with each opening covered by a flexible material and covers in integrity the cup, and the outer liner is provided with an aperture and covers in integrity the inner liner.

\* \* \* \* \*